US012662711B2

(12) United States Patent
Shih et al.

(10) Patent No.: US 12,662,711 B2
(45) Date of Patent: Jun. 23, 2026

(54) ENTEROVIRUS 71 MUTATIONS ASSOCIATED WITH DISEASE SEVERITY

(71) Applicant: ACADEMIA SINICA, Taipei (TW)

(72) Inventors: Chiaho Shih, Houston, TX (US);
Chun-Che Liao, Taipei (TW);
Chih-Shin Chang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 460 days.

(21) Appl. No.: 18/268,842

(22) PCT Filed: Dec. 20, 2021

(86) PCT No.: PCT/US2021/064392
§ 371 (c)(1),
(2) Date: Jun. 21, 2023

(87) PCT Pub. No.: WO2022/140274
PCT Pub. Date: Jun. 30, 2022

(65) Prior Publication Data
US 2024/0043944 A1 Feb. 8, 2024

Related U.S. Application Data

(60) Provisional application No. 63/128,451, filed on Dec. 21, 2020.

(51) Int. Cl.
| | |
|---|---|
| *C12Q 1/70* | (2006.01) |
| *A61K 39/125* | (2006.01) |
| *A61K 39/13* | (2006.01) |
| *A61P 31/14* | (2006.01) |
| *C12Q 1/6883* | (2018.01) |

(52) U.S. Cl.
CPC ....... *C12Q 1/701* (2013.01); *C12Q 2600/156* (2013.01)

(58) Field of Classification Search
CPC .......... A61P 25/08; A61P 31/00; A61P 31/14; C12N 2770/32334; C12N 2710/00034
See application file for complete search history.

(56) References Cited

U.S. PATENT DOCUMENTS

2010/0125918 A1 5/2010 Chen

FOREIGN PATENT DOCUMENTS

WO WO2016122403 8/2016

OTHER PUBLICATIONS

Li, R. et al., "Molecular Analysis of Virulent Determinants of Enterovirus 71", PLoS ONE, 2011, vol. 6, No. 10, article No. e26237, pp. 1-9.
Chang, S.-C. et al., "Genetic characterization of enterovirus 71 isolated from patients with severe disease by comparative analysis of complete genomes", Journal of Medical Virology, 2012, vol. 84, pp. 931-939.
Fujii, K. et al., "VP1 Amino Acid Residue 145 of Enterovirus 71 Is a Key Residue for Its Receptor Attachment and Resistance to Neutralizing Antibody during Cynomolgus Monkey Infection", Journal of Virology, 2018, vol. 92, Iss. 15, article No. e00682-18, pp. 1-17.

*Primary Examiner* — Barry A Chestnut

(57) ABSTRACT
A method of detecting severe disease-associated mutations in an enterovirus 71 (EV-A71), comprising: performing an assay on a test sample containing an EV-A71 genomic RNA, a fragment thereof or an amplicon thereof, or an EV-A71 VP1 protein or fragment thereof to detect one or more severe disease-associated mutations in the EV-A71 genomic RNA, the fragment thereof or the amplicon thereof, or the EV-A71 protein or fragment thereof, wherein the one or more mutations are selected from mutations at positions corresponding to 5' UTR nucleotide positions C580, A707, and C709 in an EV-A71 5' UTR nucleic acid sequence and at residues corresponding to A280 and E145 in an EV-A71 VP1 protein sequence.

17 Claims, 4 Drawing Sheets

Specification includes a Sequence Listing.

A

B

EV-A71
7437 bp

ENTEROVIRUS 71 MUTATIONS ASSOCIATED WITH DISEASE SEVERITY

CROSS REFERENCE

This application claims priority to U.S. Provisional Application No. 63/128,451, filed on Dec. 21, 2020, the entire content of which is hereby incorporated by reference herein.

STATEMENT REGARDING SEQUENCE LISTING

The sequence listing associated with this application is provided in text format in lieu of a paper copy and is hereby incorporated by reference into the specification. The name of the XML file containing the sequence listing is sl.xml. The XML file is 44,157 bytes; was created on Jun. 21, 2023; and is being submitted electronically via EFS-Web.

BACKGROUND

Reemergence of non-polio enterovirus is a new threat to children. Enterovirus 71 (EV-A71) is closely related to coxsackievirus, poliovirus, and hepatitis A virus. In a recent outbreak of EV-A71 in Shanghai, China, near 1000 deaths of children were reported. Infection with EV-A71 is associated with a wide range of disease severity. In mild cases, hand-foot-and-mouth disease (HFMD) is common. In severe cases, it can lead to encephalitis, acute flaccid paralysis, tachycardia, cardiopulmonary failure, and death. Studies in various animal models demonstrated that EV-A71 can target multiple tissues, including the central nerve system, and recently, the cardiopulmonary system.

The broad spectrum of disease manifestations is related in part to the differences in host immunity. See Liao et al., Journal of Virology 88, 12485-12499 (2014); Liou et al., Scientific reports 6, 31151 (2016); and Liou et al., J. Biomed. Sci. 26 (1): 93 (2019). In addition, a research topic has been whether sequence variation of EV-A71 could contribute to the different degrees and tropisms of pathogenesis in vivo. Previous studies reported various viral mutations associated with disease severity in different human cases or mouse models. For example, amino acid 145E of VP1 is the most well documented mutation important for viral replication and pathogenesis in mouse models. See, Chua et al., Journal of General Virology 89, 1622 (2008); Huang et al., Virology 422, 132 (2012); Kobayashi et al., J Virol., 92(15):e00681-18 (2018); and Tee et al., PLoS Pathog. 15(11):e1007863 (2019). Similarly, in a monkey model, VP1-145E viruses can induce neurological symptoms, and it was suggested that VP1-145E has a replication advantage for the virus in the monkeys. See, Fujii et al., J Virol., 92(15):e00682-18 (2018). In contrast to both mouse and monkey models, VP1-145E does not appear to be associated with severe sequelae using human samples. Instead, amino acids 145Q had been observed in 2 out of 9 severe diseases. See, Chang et al., Journal of Medical Virology 84, 931 (2012). In addition, 145Q, 145G, and 145R had been associated with virulent phenotype by analyzing 25 severe cases and 31 mild cases from the GenBank database. See, Li et al. PLoS One 6, e26237 (2011). It has remained a discrepancy between mouse models and human samples whether VP1-145E and disease severity are associated with each other Amino acid 145 of VP1 is generally thought to be involved in the binding between EV-A71 and its entry receptor SCARB2 (scavenger receptor class B, member 2).

See, Kobayashi et al., J Virol., 92(15):e00681-18 (2018); and Fujii et al., J Virol., 92(15):e00682-18 (2018).

At present, there is no FDA-approved therapeutics for EV-A71. Current treatment remains supportive, and no antivirals are commercially available. Early diagnosis of high-risk children is the key to successful patient care.

SUMMARY

In one aspect, described herein is a method of detecting severe disease-associated mutations in an enterovirus 71 (EV-A71), comprising: performing an assay on a test sample containing an EV-A71 genomic RNA, a fragment thereof or an amplicon thereof, or an EV-A71 VP1 protein or fragment thereof to detect one or more severe disease-associated mutations in the EV-A71 genomic RNA, the fragment thereof or the amplicon thereof, or the EV-A71 protein or fragment thereof, wherein the one or more mutations are selected from mutations at positions corresponding to 5' UTR nucleotide positions C580, A707, and C709 in an EV-A71 5' UTR nucleic acid sequence and at residues corresponding to A280 and E145 in an EV-A71 VP1 protein sequence.

In some embodiments, the mutations are C580U, A707G, C709U, A280T, and E145(non-E). In some embodiments, the assay detects the severe disease-associated mutations in the genome of the EV-A71 or mutated amino acids in proteins resulting from the severe disease-associated mutations. In some embodiments, the assay includes an immune assay or PCR-based amplification followed by a sequencing assay. In some embodiments, the test sample is prepared from a biological sample obtained from a subject infected with the EV-A71. In some embodiments, the biological sample contains a body fluid, tissue, or cell. The sample can be a throat or nose swab, cerebral spinal fluid (CSF) sample, blood sample, serum sample, plasma sample, tear sample, urine sample, nasal excretion sample, sputum sample, sperm sample, or feces sample.

In another aspect, provided herein is a method of assessing risk of developing a severe disease in a subject infected with an enterovirus 71 (EV-A71), comprising: obtaining a test sample containing an EV-A71 genomic RNA, a fragment thereof or an amplicon thereof, or an EV-A71 VP1 protein or fragment thereof, wherein the test sample is prepared from a subject infected with the EV-A71; and detecting in the test sample the presence of one or more of severe disease-associated mutations in the EV-A71 genomic RNA, the fragment thereof or the amplicon thereof, or the EV-A71 VP1 protein or fragment thereof, wherein the one or more mutations are selected from mutations at positions corresponding to 5' UTR nucleotide positions C580, A707, and C709 in an EV-A71 5' UTR nucleic acid sequence and at residues corresponding to A280 and E145 in an EV-A71 VP1 protein sequence, wherein the presence of one or more of the mutations indicates a higher risk of developing a severe disease in the subject.

In yet another aspect, a method of treating a subject infected with an enterovirus 71 (EV-A71) is described herein. The method comprises: obtaining a test sample containing an EV-A71 genomic RNA, a fragment thereof or an amplicon thereof, or an EV-A71 VP1 protein or fragment thereof, wherein the test sample is prepared from a biological sample obtained from a subject infected with the EV-A71; and detecting in the test sample the presence of one or more of severe disease-associated mutations in the EV-A71 genomic RNA, the fragment thereof or the amplicon thereof, or the EV-A71 VP1 protein or fragment thereof, wherein the one or more mutations are selected from mutations at positions corresponding to 5' UTR nucleotide positions C580, A707, and C709 in an EV-A71 5' UTR nucleic acid sequence and at residues corresponding to A280 and E145 in an EV-A71 VP1 protein sequence; and administering a treatment or treatment regimen for decreasing risk of development of a severe disease in the subject.

In any of the above methods, the one or more mutations can be selected from C580U, A707G, C709U, A280T, and E145(non-E). In some embodiments, any one of the mutations, any combination of two, three, or four of the mutations, or all five mutations can be detected. In some embodiments, the assay detects the severe disease-associated mutations in the genome of the EV-A71 or mutated amino acids in proteins resulting from the severe disease-associated mutations. In some embodiments, the detecting step is carried out with an immune assay or PCR-based amplification followed by a sequencing assay. In some embodiments, the biological sample contains a body fluid, tissue, or cell. The biological sample can be a throat or nose swab, cerebral spinal fluid (CSF) sample, blood sample, serum sample, plasma sample, tear sample, urine sample, nasal excretion sample, sputum sample, sperm sample, or feces sample. In some embodiments, the severe disease is myoclonic jerks, meningitis, encephalitis, acute flaccid paralysis, tachycardia, pulmonary edema, cardiopulmonary failure, or death.

The details of one or more embodiments are set forth in the accompanying drawing and the description below. Other features, objects, and advantages of the embodiments will be apparent from the description and drawing, and from the claims.

DETAILED DESCRIPTION

Figure 1:
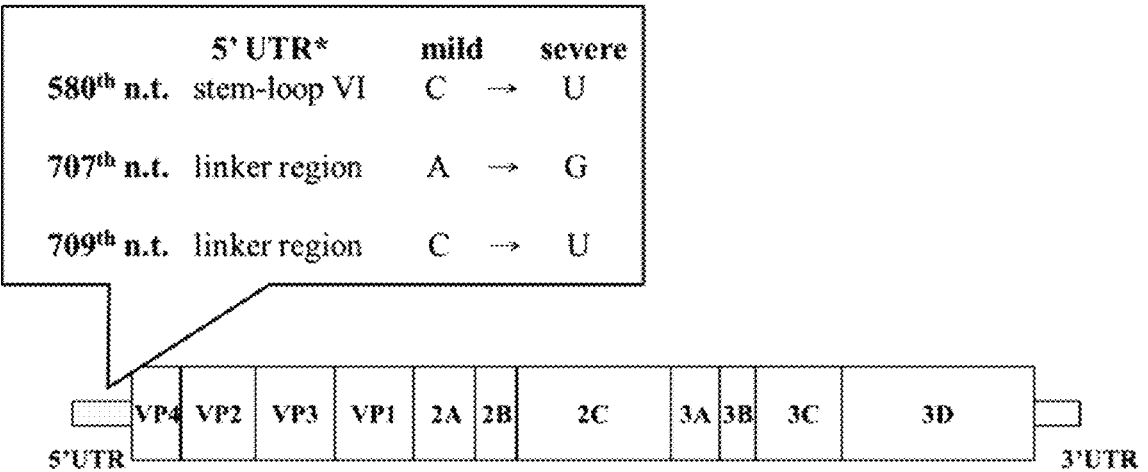
FIG. 1 is a schematic representation showing association of disease severity with three point mutations in the 5' UTR in the EV-A71 genome. Genomic sequences of EV-A71 from mild cases (n=36) and severe cases (n=27) were compared. Three point mutations were found in the 5' UTR: C580U, A707G, and C709U. In this 2D diagram of RNA fold, nt 580 is within stem-loop VI, and nt 707 and 709 are in the linker region.
Figure 1:
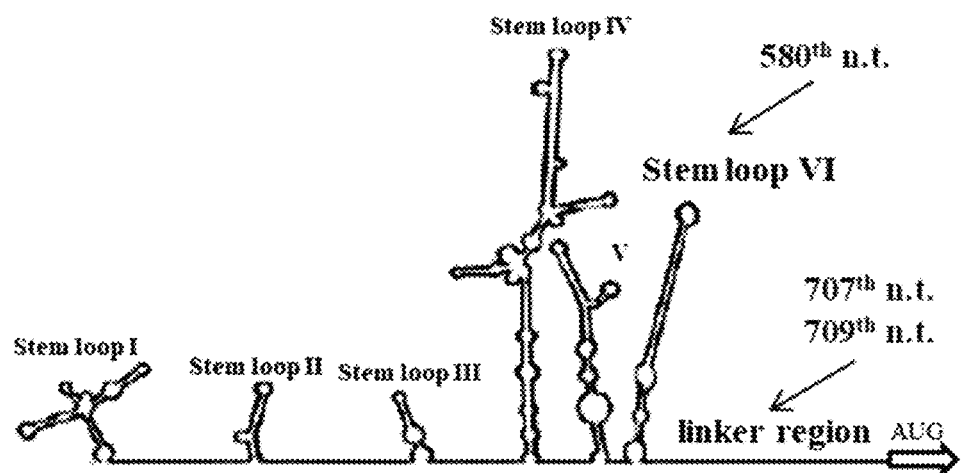

It was unexpectedly discovered that five EV-A71 mutations are associated with severe diseases in patients, including (1) the 5' UTR mutations C580U, A707G, and C709U; (2) a VP1 alanine-to-threonine mutation at position 280

(280T), and (3) a VP1 glutamic acid-to-(non-glutamic acid) mutation at position 145 (145(non-E).

These mutations can be used to assess the risk of developing a severe disease in a subject infected with an EV-A71, and treating a subject infected with an EV-A71.

The positions of the mutations correspond to 5' UTR nucleotide positions C580, A707, and C709 in an EV-A71 5' UTR nucleic acid sequence and residues A280 and E145 in an EV-A71 VP1 protein sequence. Any one of the mutations, any combination of two, three, or four of the mutations, or all five mutations can be detected.

The EV-A71 5' UTR nucleic acid sequence can be any of the following sequences: GenBank Accession Nos. MT360921, MT360922, MT360927, MT360935, MT360937, MT360938, or MT360943. The EV-A71 VP1 protein sequence can be any of the following sequences: GenBank Accession Nos: MT348284, MT348285, MT348286, MT348287, MT348288, MT348289, MT348291, MT348292, MT348293, MT348294, MT348295, MT348296, MT348297, MT348298, MT348299, MT348300, MT348301, MT348302, MT348303, MT348304, MT348305, MT348306, MT348321, MT348341, MT348342, or MT348346.

Various methods known in the art or described below can be performed to detect these mutations. A biological sample obtained from a subject infected with EV-A71 can be used directly or further processed to detect the mutations. For example, nucleic acid molecules from the sample can be extracted, optionally amplified by PCR (e.g., RT-PCR), and sequenced to detect the mutations. Other techniques including nucleic acid hybridization can also be used. Virus preparation can be carried out using procedures known in the art. See, Liao et al., Journal of Virology 88, 12485-12499, (2014); Liou et al., Scientific Reports 6, 31151 (2016); Liou et al., J. Biomed. Sci. 26 (1): 93 (2019); and Chang et al., Scientific Reports 9 (1), 11108 (2019). The mutations in the VP1 protein can be detected directly in the protein or in the genomic nucleic acid Immunoassays, such as those using an antibody that specifically binds to a mutated VP1 protein, can be carried out to detect the mutations in VP1. The biological sample can contain a bodily fluid, tissue, or cell sample, e.g., throat or nose swab, cerebral spinal fluid (CSF) sample, blood sample, serum sample, plasma sample, tear sample, urine sample, nasal excretion sample, sputum sample, sperm sample, or feces sample.

If a subject is infected with an EV-A71 virus containing one or more of the mutations, the subject has a higher risk of developing a severe disease such as myoclonic jerks, meningitis, encephalitis, acute flaccid paralysis, tachycardia, pulmonary edema, cardiopulmonary failure, or death. Therefore, detection of the mutations can guide treatment decisions. Preferably, presence or absence of the mutations should be analyzed as soon as possible. For example, the analysis should be performed when a patient is first admitted to the hospital. A patient infected by an EV-A71 containing one or more of the mutations described herein may be checked into the ICU for closer monitoring and care. Further, as discussed below, a VP1-145(non-E) mutation could be associated with an increased risk for disease severity via the PSGL-1 receptor-mediated entry pathway. A VP1-280T mutation could contribute to virulence via a de novo created hydrogen bonding with the highly conserved VP2-139T residue, leading to efficient infection via the SCARB2 receptor-mediated entry pathway. If either mutation is present, treatments aimed at blocking PSGL-1 receptor binding, SCARB binding or VP1-VP2 interaction may be attempted.

Also provided herein is a kit containing reagents for detecting the presence or absence of the mutations described herein. Such kit can be used to identify high-risk patients and guide medical care. The kit can include PCR primers, oligonucleotide probes, or antibodies aimed at detecting one or more of the mutations described herein.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are herein incorporated by reference in their entirety.

Example 1: EV-A71 Mutations Associated with Severe Diseases

By PCR amplification and sequencing, the sequences of the 5' UTR and the capsid protein VP1 in EV-A71 viral genomes isolated from clinical samples of 36 mild and 27 severe patients were analyzed. Full-length sequences of viral genomes were also obtained from 7 severe and 8 mild patients. These patient samples were collected during an EV-A71 outbreak in Taiwan in 2008. See, e.g., Liao et al., Journal of virology 88, 12485-12499, (2014).

Except for within the 5' UTR and VP1, no mutation associated with disease severity, based on the full-length genome sequences from 7 severe and 8 mild cases, was identified. At the 5' UTR (nt 1-747), three mutations, C580U, A707G, C709U, were found to occur frequently in severe patients (7/27) (Chi-square p=0.006; Fisher Exact test p=0.0166). See FIG. 1 and Table 1. The mutation C580U falls within the stem-loop VI structure and remains to be investigated whether it could affect the cap-independent translation via the internal ribosomal entry site (IRES). See FIG. 1. Mutations A707G and C709U are located in the linker region between the stem-loop VI and the AUG initiation codon. See FIG. 1.

In the literature, at least 10 mutations at the 5' UTR have been associated with disease severity, including those at positions 150, 158, 241, 272, 488, 494, 571, 579, 606, and 700. None of these mutations in previous reports overlapped with the mutations at positions 580, 707, and 709.

TABLE 2

Statistical analysis of severity-associated VP1 mutations

| | VP1-145th a.a. | | | VP1-280th a.a. | |
|---|---|---|---|---|---|
| | E (Glu) | non-E* | | A (Ala) | T (Thr)** |
| Mild cases (36) | 12 (33%) | 24 (67%) | Mild cases (36) | 35 (97%) | 1 (3%) |
| Severe cases (27) | 1 (4%) | 26 (96%) | Severe cases (27) | 20 (74%) | 7 (26%) |
| Genbank (3653) | 3172 (87%) | 481 (13%) | Genbank (3231) | 3199 (99%) | 20 (0.6%) |

*Chi-square (χ2= 8.2708) p = 0.004; Fisher's Exact Test (p = 0.0043), odds ratio = 13 (95% CI = 1.5697~107.6669).
**Chi-square (χ2= 5.9063) p = 0.015; Fisher's Exact Test (p = 0.036), odds ratio = 10 (95% CI = 1.1247~88.9097).

The results of 145E in mild cases and 145(nonE) in severe cases described here are exactly opposite to the previous results from animal models. For example, VP1-145E has been shown to contribute to viremia, lethality or pathogenesis in animal models. See, Chua et al., Journal of General Virology 89, 1622 (2008); Huang et al., Virology 422, 132 (2012); Kobayashi et al., J Virol., 92(15):e00681-18 (2018); and Tee et al., PLoS Pathog. 15(11):e1007863 (2019). In the animal models, the mutations could reflect mouse-specific adaptive mutations, rather than bona fide naturally occurring mutations in human patients. Indeed, as shown in the above-discussed data, VP1-145E does not appear to be associated with severe cases in human patients. while VP1-145E has always been shown to be a virulence determinant in mice. Also see, Li et al., PloS One 6, e26237 (2011). Here, it was discovered that VP1-145(non-E) is exclusively associated with human severe cases (26/27, 96%). See Table 2.

GenBank database collects EV-A71 sequences (n=3653, as of April, 2020) deposited at different times from different countries worldwide. For most of these GenBank sequences, no information is available regarding the degree of disease severity of their source patients from the sequence-donating laboratories. Here, these pooled and non-stratified GenBank sequences collectively were considered as a convenient baseline for comparison with our data. It is striking to note that VP1-145(non-E) occurred only at a baseline frequency of 13% (481/3653) in the GenBank database, including 145Q (256/3653, 7%), 145G (197/3653, 5.4%), 145A (16/3653, 0.4%) and 145R (5/3653, 0.1%). See Table 2. In

TABLE 1

Statistical analysis of severity-associated UTR mutations

| | 5'-UTR-580th n.t. | | 5'-UTR-707th n.t. | | 5'-UTR-709th n.t. | |
|---|---|---|---|---|---|---|
| | C | U* | A | G* | C | U* |
| Mild cases (36) | 35 (97%) | 1 (3%) | 35 (97%) | 1 (3%) | 35 (97%) | 1 (3%) |
| Severe cases (27) | 20 (74%) | 7 (26%) | 20 (74%) | 7 (26%) | 20 (74%) | 7 (26%) | p = 0.006, value referring to the Chi-square statistical analysis ($\chi^2$ = 7.4574) of the * columns. Fisher's Exact Test (p = 0.0166), odds ratio = 12.25 (95% CI = 1.4041~106.8733).

Figure 2:
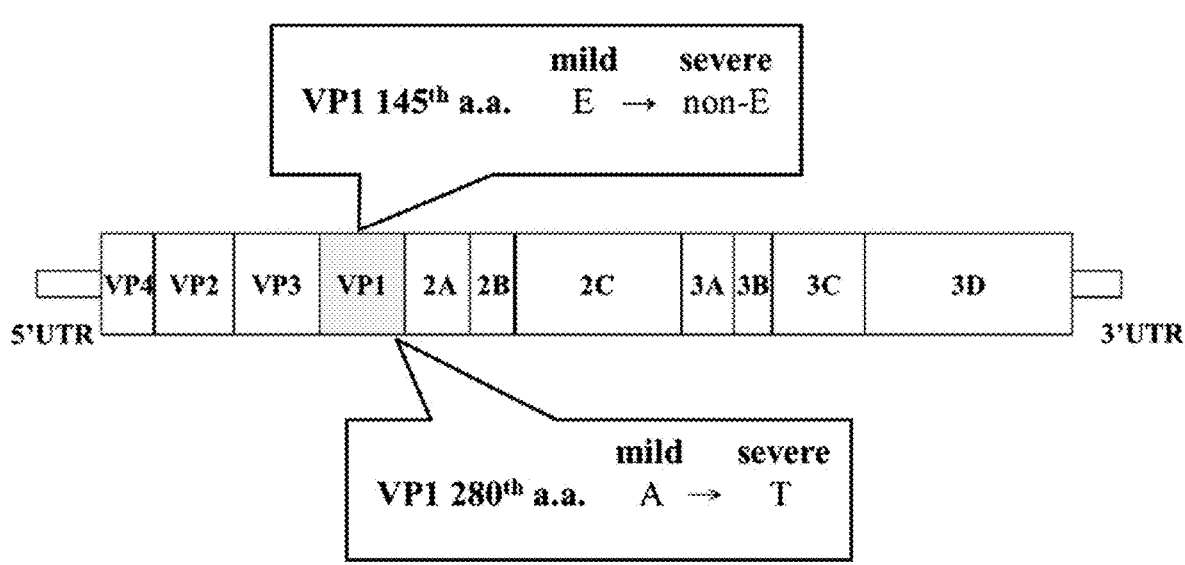
FIG. 2 is a schematic representation showing capsid protein VP1-145(non-E) and VP1-280T are associated with disease severity in EV-A71 infected patients.

Capsid protein VP1 (891 nt) has been used as a standard reference for genotyping. VP1-145(non-E) was found to be strongly associated with severe cases (26/27, 96%), while VP1-145E was found to be associated with mild cases (12/36, 33%) (Chi-square p=0.004; Fisher Exact test p=0.0043). See FIG. 2 and Table 2. These 26 VP1-145(non-E) severe cases included 145Q (16), 145G (9), and 145A (1). Neither 145Q alone nor 145G alone was determined to be associated with severe cases with statistical significance.

contrast, VP1-145(non-E) occurred at a 7.4-fold higher frequency (96%, 26/27) in the severe cases analyzed here. In general, EV-A71 infection caused mainly subclinical or mild symptoms, such as herpangina and HFMD. Occasionally, it could cause severe disease manifestations, such as neurological disorders, cardiopulmonary failure, and death. The vast majority of VP1 sequences in the GenBank contained a VP1-145E (3172/3653, 87%). See Table 2. This fact supports the idea that VP1-145E is preferentially associated with mild cases, which is entirely consistent with current knowledge about the predominant subclinical or mild symptoms in EV-A71 natural infection.

Unexpectedly, among those 7 severe cases containing 5' UTR mutations, 6 out of 7 cases contained a novel alanine-to-threonine mutation at the VP1 position 280 (A280T). See FIG. 2. 99% (3199/3231) of VP1 sequences in the GenBank were found to contain VP1-280A, and only 0.6% were found to contain VP1-280T (20/3231). See Table 2. In contrast, 22% (6/27) in the severe cases in this study were found to contain VP1-280T. See Table 2. This frequency of occurrence (22%) is near 37-fold higher than the baseline frequency (0.6%) found in the GenBank sequences.

EV-A71 can bind to SCARB2 or PSGL-1 (P-selectin glycoprotein ligand-1) receptors for entry (Yamayoshi et al., 2009; Nishimura et al., 2009). See, Yamayoshi et al., Nature Medicine 15, 798-801(2009); and Nishimura et al., PLoS Pathog. 9(7):e1003511 (2013). The structure of the binding complex of EV-A71 and SCARB2 has recently been resolved by cryoEM at 3.4-angstron resolution. See, Zhou et al., Nat Microbiol. 4(3):414-419 (2019). Coincidentally, amino acid 280 of VP1 is located in the immediate neighborhood of the contact site between VP2 and the SCARB2 receptor. A close-up view at the contact site revealed the interaction between a VP2 loop turn and the α7 helix of SCARB2. This loop turn of VP2 may be stabilized by a web-like interaction structure, which consists of multiple hydrogen bonds between VP1-281G, VP1-282D and VP2 135V-141T. The VP1 mutation from alanine to threonine at amino acid 280 could generate an extra H-bond between VP1-280T and VP2-139T, which in turn could enhance the interaction between the virus and its SCARB2 entry receptor. According to this complex structure, VP1-145 is far away from the contact site between SCARB2 and VP2.

Figure 3:
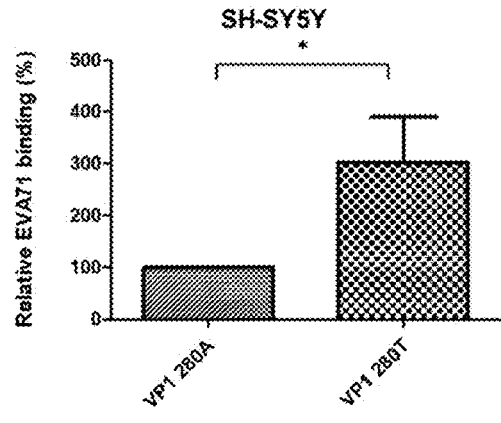
FIG. 3 is a set of graphs and images showing that EV-A71 enterovirus VP1-280T bound to a human neuroblastoma cell line SH-SY5Y better than virus VP1-280A. (A) Binding assays. HTB10: a human neuroblastoma cell line, RD: a human rhabdomyosarcoma cell line. (B) Comparisons of SCARB2 expression levels among different cells infected with viruses VP1-280T vs. VP1-280A using Western blot analysis with an anti-SCARB2 antibody. IMR32: human neuroblastoma cell line; 3T3 and L929: mouse fibroblast cell lines; Mock: uninfected culture; GAPDH: an internal control.
Figure 3:
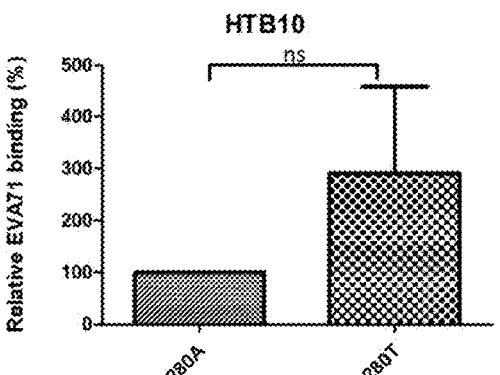
Figure 3:
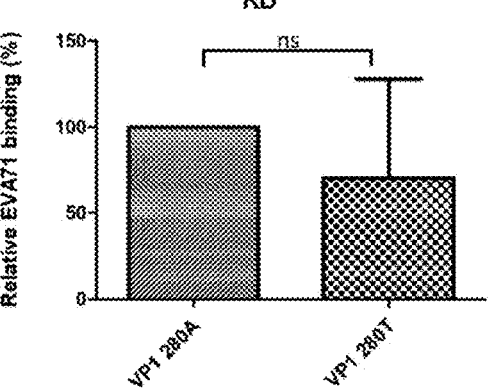
Figure 3:

The binding activities between VP1-280A and VP1-280T viruses were compared with human rhabdomyosarcoma cell line RD, human neuroblastoma cell lines HTB10 and SH-SY5Y. See FIG. 3(A). No difference in their respective binding activities was detected between VP1-280A and its congenic (isogenic) VP1-280T using HTB10 or RD cells. However, VP1-280T appeared to bind better to SH-SY5Y cells than VP1-280A. The expression levels of SCARB2 were similar in various host cell lines infected with VP1-280T or VP1-280A by Western blot analysis. See FIG. 3(B).

The 5' UTR is known to contain cis-elements important for both IRES-mediated cap-independent translation and the replication origin for genome multiplication. While nucleotide 580 falls within the stem-loop VI and IRES, nucleotides 707 and 709 are in the linker region between IRES and the first AUG initiation codon. To investigate whether these novel 5' UTR mutations have any functional significance in IRES-mediated translation, reporter assays in human RD cells were conducted (data not shown). Although no significant difference in the reporter activities between the WT and mutant 5' UTR, it remains possible that these mutations could play a role in genome replication in viral life cycle.

The potential linkage relationship of the severity-associated mutations is shown in Table 3. Among the 7 severe patients containing 5' UTR mutations, 6 out of 7 severe cases also contain a VP1-A280T mutation.

TABLE 3

Linkage of severity-associated mutations

| | 5' UTR nucleotide # | | | VP1 amino acid # | |
|---|---|---|---|---|---|
| | 580 | 707 | 709 | 145 | 280 |
| No. F1 | U | G | U | Gly | Thr |
| No. F6 | U | G | U | Gly | Ala |
| No. F7 | U | G | U | Gly | Thr |
| No. F9 | U | G | U | Gln | Thr |
| No. F17 | U | G | U | Glu | Thr |
| No. F22 | U | G | U | Gln | Thr |
| No. F23 | U | G | U | Gln | Thr |
| No. 1 | C | A | C | Gln | Ala |
| No. 5 | C | A | C | Gln | Ala |
| No. 6 | C | A | C | Gln | Ala |
| No. 26 | C | A | C | Gly | Ala |
| No. F2 | C | A | C | Gly | Ala |
| No. F3 | C | A | C | Gln | Ala |
| No. F4 | C | A | C | Gln | Ala |
| No. F5 | C | A | C | Gln | Ala |
| No. F8 | C | A | C | Gly | Ala |
| No. F10 | C | A | C | Gln | Ala |
| No. F11 | C | A | C | Gln | Ala |
| No. F12 | C | A | C | Gly | Ala |
| No. F13 | C | A | C | Gln | Ala |
| No. F14 | C | A | C | Gln | Ala |
| No. F15 | C | A | C | Gln | Ala |
| No. F16 | C | A | C | Gln | Ala |
| No. F18 | C | A | C | Gly | Ala |
| No. F19 | C | A | C | Gln | Ala |
| No. F20 | C | A | C | Gly | Ala |
| No. F21 | C | A | C | Ala | Ala |

Example 2: Materials and Methods

Ethics Statement

EV71 clinical isolates were kindly provided by Section of Clinical Virology and Molecular Diagnosis, Department of Laboratory Medicine, Changhua Christian Hospital, Taiwan. Biosafety Committee approval number BSF 005 20080030 from Academia *Sinica, Taiwan.*

Disease Severity

Clinical presentations of mild cases included herpangina or HFMD only. In addition to herpangina and HFMD, symptoms of severe cases included myoclonic jerks, meningitis, encephalitis, acute flaccid paralysis, pulmonary edema, cardiopulmonary failure, and death.

Preparations of Cells and Viruses

Human rhabdomyosarcoma (RD) cells (ATCC CCL-136) were cultured in DMEM (Dulbecco's modified Eagle medium) with 10% fetal bovine serum (FBS; HyClone) and 1% penicillin-streptomycin. Viral strains of EV-A71 were isolated from throat swabs of patients by the Section of Clinical Virology and Molecular Diagnosis, Department of Laboratory Medicine, Changhua Christian Hospital, Taiwan. Virus preparation was as described previously. See, Liao et al., Journal of Virology 88, 12485-12499, (2014); Liou et al., Scientific Reports 6, 31151 (2016); Liou et al., J. Biomed. Sci. 26 (1): 93 (2019); and Chang et al., Scientific Reports 9 (1), 11108 (2019).

RT-PCR and Sequencing

Figure 4:
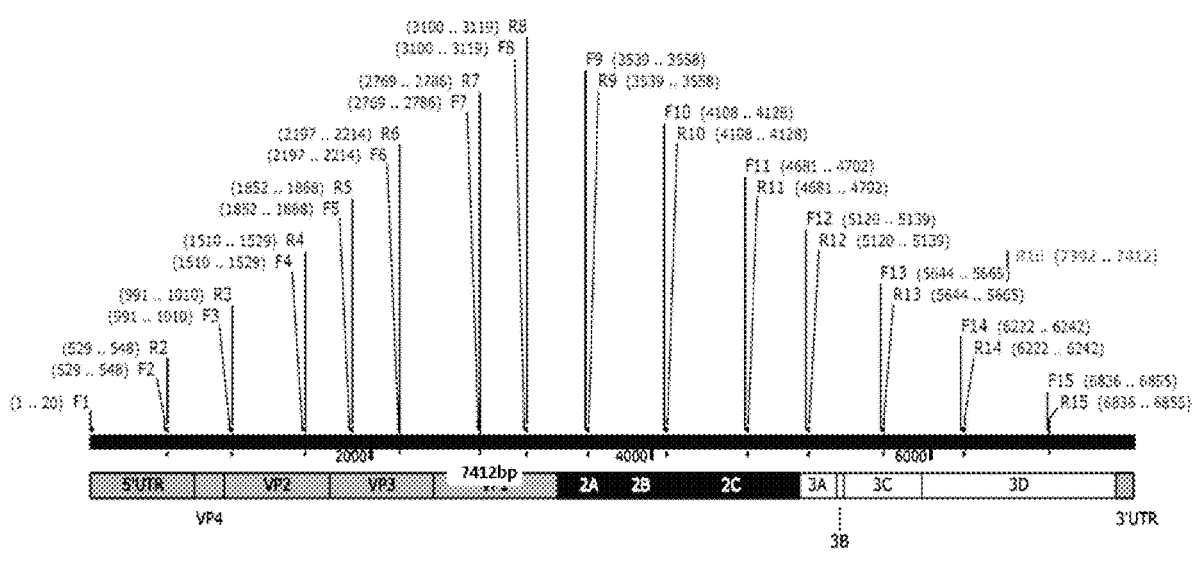
FIG. 4. Is a schematic representation showing sequencing strategy of the full-length EV-A71 viral genome and the locations of sequencing primers.

Procedures for RT-PCR were as described elsewhere. See Liao et al., Journal of Virology 88, 12485-12499, (2014). The sequencing strategy and primer sequences are shown in FIG. 4 and Table 4. 5'UTR and VP1 fragments were amplified using PCR primer pairs F1 and R4, F5 and R10, respectively. PCR-amplified DNA fragments were sequenced using the sequencing primers listed in Table 4 with ABI 3730XL DNA analyser (PE Applied Biosystems, Foster City, CA). Multiple sequence alignment was performed using the Clustal W multiple alignment program of the MegAlign software version 7.1.0 (DNASTAR, Madison, WI, USA).

Binding Assay

SH-SY5Y, HTB-10 and RD cells were seeded in 6 well plate ($1\times10^6$/well) and cultured with Dulbecco's Modified Eagle medium (DMEM; Gibco) with 10% fetal bovine serum (FBS; Hyclone) and 1% penicillin-streptomycin (Gibco) at 37° C. overnight. Culture medium was removed, and cells were washed once with phosphate buffer saline (PBS) before incubation with EV-A71 virus VP1-280A or VP1-280T (M.O.I=10) at 4° C. for 1 hour. Unbound virus was removed by washing with PBS three times. Total RNAs in cells were extracted with a WelPrep cell/tissue RNA kit (Wel-GENE) and used for reverse transcription by a High-Capacity cDNA reverse transcription kit (Applied Biosystems). The synthetic cDNA was subjected to real-time quantitative PCR (qPCR) analysis by an ABI 7500 system with a Power SYBR green PCR master kit (both from Applied Biosystems). Specific primers for VP1 were CTAGAGGGTACCACCAATCC (forward; SEQ ID NO: 31) and AACCTGGCCAGTAGGAGT (reverse; SEQ ID NO: 32). The primer sequences of GAPDH (glyceraldehyde-3-phosphate dehydrogenase) were used as the internal control: ACCCAGAAGACTGTGGATGG (forward; SEQ ID NO: 33) and TCAGCTCAGGGATGACCTTG (reverse; SEQ ID NO: 34). The amounts of viral RNA were normalized to the levels of GAPDH.

TABLE 4

Sequencing primers

| Name | | Sequence |
|------|---|----------|
| F1 | SEQ ID NO: 1 | TTAAAACAGCCTGTGGGT |
| F2 | SEQ ID NO: 2 | AACTCTGCAGCGGAACCGAC |
| R2 | SEQ ID NO: 3 | GTCGGTTCCGCTGCAGAGTT |
| F3 | SEQ ID NO: 4 | GTGGCACAACTCACCATTGG |
| R3 | SEQ ID NO: 5 | CCAATGGTGAGTTGTGCCAC |
| F4 | SEQ ID NO: 6 | CGGACCAATAACTGTGCCAC |
| R4 | SEQ ID NO: 7 | GTGGCACAGTTATTGGTCCG |
| F5 | SEQ ID NO: 8 | TTGTGTCAAGTGGAGAC |
| R5 | SEQ ID NO: 9 | GTCTCCACTTGACACAA |
| F6 | SEQ ID NO: 10 | CTACAATCATCTGTCACC |
| R6 | SEQ ID NO: 11 | GGTGACAGATGATTGTAG |
| F7 | SEQ ID NO: 12 | GGATATAGACATAACTGG |
| R7 | SEQ ID NO: 13 | CCAGTTATGTCTATATCC |
| F8 | SEQ ID NO: 14 | CTTGAATATGGAGCGTGTCC |
| R8 | SEQ ID NO: 15 | GGACACGCTCCATATTCAAG |

TABLE 4-continued

Sequencing primers

| Name | | Sequence |
|------|---|----------|
| F9 | SEQ ID NO: 16 | GAAAGCACTATCCAGTCAGC |
| R9 | SEQ ID NO: 17 | GCTGACTGGATAGTGCTTTC |
| F10 | SEQ ID NO: 18 | GATATGGCGAGTGCCGCCAAG |
| R10 | SEQ ID NO: 19 | CTTGGCGGCACTCGCCATATC |
| F11 | SEQ ID NO: 20 | CCACCAATGGCTTCTCTTGAAG |
| R11 | SEQ ID NO: 21 | CTTCAAGAGAAGCCATTGGTGG |
| F12 | SEQ ID NO: 22 | CAGACGCTATTAGCGATCTC |
| R12 | SEQ ID NO: 23 | GAGATCGCTAATAGCGTCTG |
| F13 | SEQ ID NO: 24 | GATATCACCAAGTTCATTCCAG |
| R13 | SEQ ID NO: 25 | CTGGAATGAACTTGGTGATATC |
| F14 | SEQ ID NO: 26 | GATGAGCATGGAGGAAGCGTG |
| R14 | SEQ ID NO: 27 | CACGCTTCCTCCATGCTCATC |
| F15 | SEQ ID NO: 28 | CAATGATCAACAACATCATC |
| R15 | SEQ ID NO: 29 | GATGATGTTGTTGATCATTG |
| R16 | SEQ ID NO: 30 | GCTATTCTGGTTATAACAAAT |

Bioinformatics

Discovery Studio Visualizer was from Dassault Systèmes BIOVIA Corp (2015), San Diego, CA USA. The PyMol software was from PyMOL Molecular Graphics System, Version 1.8 Schrödinger, LLC.

Statistical Analysis

Relative EV-A71 binding assays were analyzed by Student's t test. Mutation frequencies of viral genome were analyzed by the Chi-square test and the Fisher's Exact test. *$P<0.05$; **$P<0.001$.

GenBank Accession Numbers

VP1 sequences: MT348284-MT348346; 5' UTR sequences: MT360921-MT360983; full-length EV-A71 genome: MT360984-MT360998.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. A method of detecting severe disease-associated mutations in an enterovirus 71 (EV-A71), comprising:

performing an assay on a test sample containing an EV-A71 genomic RNA, a fragment thereof or an amplicon thereof, or an EV-A71 VP1 protein or fragment thereof to detect one or more severe disease-associated mutations in the EV-A71 genomic RNA, the fragment thereof or the amplicon thereof, or the EV-A71 protein or fragment thereof, wherein the one or more mutations are selected from mutations at positions corresponding to 5' UTR nucleotide positions C580U, A707G, and C709U in an EV-A71 5' UTR nucleic acid sequence and at residues corresponding to A280T in an EV-A71 VP1 protein sequence.

2. The method of claim 1, wherein the assay detects the one or more severe disease-associated mutations in the genome of the EV-A71 or one or more mutated amino acids in proteins resulting from the one or more severe disease-associated mutations.

3. The method of claim 2, wherein the assay is an immune assay or a PCR-based amplification followed by a sequencing assay.

4. The method of claim 1, wherein the test sample is prepared from a biological sample from a subject infected with the EV-A71.

5. The method of claim 4, wherein the biological sample contains a body fluid, tissue, or cell.

6. The method of claim 5, wherein the sample is a throat swab, cerebral spinal fluid (CSF) sample, blood sample, serum sample, plasma sample, tear sample, urine sample, nasal excretion sample, sputum sample, sperm sample, or feces sample.

7. A method of assessing risk of developing a severe disease in a subject infected with an enterovirus 71 (EV-A71), comprising:

obtaining a test sample containing an EV-A71 genomic RNA, a fragment thereof or an amplicon thereof, or an EV-A71 VP1 protein or fragment thereof, wherein the test sample is prepared from a biological sample from a subject infected with the EV-A71; and detecting in the test sample the presence of one or more of severe disease-associated mutations in the EV-A71 genomic RNA, the fragment thereof or the amplicon thereof, or the EV-A71 VP1 protein or fragment thereof, wherein the one or more mutations are selected from mutations at positions corresponding to 5' UTR nucleotide positions C580U, A707G, and C709U in an EV-A71 5' UTR nucleic acid sequence and at residues corresponding to A280T in an EV-A71 VP1 protein sequence;

wherein the presence of one or more of the mutations indicates a higher risk of developing a severe disease in the subject.

8. The method of claim 7, wherein the detecting step detects the one or more severe disease-associated mutations in the genome of the EV-A71 or one or more mutated amino acids in proteins resulting from the one or more severe disease-associated mutations.

9. The method of claim 8, wherein the detecting step includes performing an immune assay or a PCR-based amplification followed by a sequencing assay.

10. The method of claim 7, wherein the test sample is prepared from a biological sample from the subject that contains a body fluid, tissue, or cell.

11. The method of claim 10, wherein the sample is a throat swab, cerebral spinal fluid (CSF) sample, blood sample, serum sample, plasma sample, tear sample, urine sample, nasal excretion sample, sputum sample, sperm sample, or feces sample.

12. A method of treating a subject infected with an enterovirus 71 (EV-A71), comprising:

obtaining a test sample containing an EV-A71 genomic RNA, a fragment thereof or an amplicon thereof, or an EV-A71 VP1 protein or fragment thereof, wherein the test sample is prepared from a biological sample from a subject infected with the EV-A71; and detecting in the test sample the presence of one or more of severe disease-associated mutations in the EV-A71 genomic RNA, the fragment thereof or the amplicon thereof, or the EV-A71 VP1 protein or fragment thereof, wherein the mutations are selected from mutations at positions corresponding to 5' UTR nucleotide positions C580U, A707G, and C709U in an EV-A71 5' UTR nucleic acid sequence and at residues corresponding to A280T in an EV-A71 VP1 protein sequence; and administering a treatment or treatment regimen for decreasing risk of development of a severe disease in the subject.

13. The method of claim 12, wherein the assay detects the one or more severe disease-associated mutations in the genome of the EV-A71 or mutated amino acids in proteins resulting from the one or more severe disease-associated mutations.

14. The method of claim 12, wherein the detecting step is carried out with an immune assay or PCR-based amplification followed by a sequencing assay.

15. The method of claim 12, wherein the biological sample contains a body fluid, tissue, or cell.

16. The method of claim 15, wherein the biological sample is a throat swab, cerebral spinal fluid (CSF) sample, blood sample, serum sample, plasma sample, tear sample, urine sample, nasal excretion sample, sputum sample, sperm sample, or feces sample.

17. The method of claim 12, wherein the severe disease is myoclonic jerks, meningitis, encephalitis, acute flaccid paralysis, tachycardia, pulmonary edema, cardiopulmonary failure, or death.

\* \* \* \* \*

24

SEQUENCE LISTING

<160> NUMBER OF SEQ ID NOS: 34

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1
ttaaaacagc ctgtgggt                                                    18

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
aactctgcag cggaaccgac                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gtcggttccg ctgcagagtt                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
gtggcacaac tcaccattgg                                                  20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ccaatggtga gttgtgccac                                                  20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
cggaccaata actgtgccac                                                  20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gtggcacagt tattggtccg                                                 20

<210> SEQ ID NO 8
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 8
ttgtgtcaag tggagac                                                    17

<210> SEQ ID NO 9
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 9
gtctccactt gacacaa                                                    17

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 10
ctacaatcat ctgtcacc                                                   18

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
ggtgacagat gattgtag                                                   18

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 12
ggatatagac ataactgg                                                   18

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
ccagttatgt ctatatcc                                                   18

-continued

```
<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
cttgaatatg gagcgtgtcc                                            20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ggacacgctc catattcaag                                            20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
gaaagcacta tccagtcagc                                            20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gctgactgga tagtgctttc                                            20

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
gatatggcga gtgccgccaa g                                          21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
cttggcggca ctcgccatat c                                          21

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide
```

-continued

<400> SEQUENCE: 20
ccaccaatgg cttctcttga ag                                                          22

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
cttcaagaga agccattggt gg                                                          22

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
cagacgctat tagcgatctc                                                             20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
gagatcgcta atagcgtctg                                                             20

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 24
gatatcacca agttcattcc ag                                                          22

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
ctggaatgaa cttggtgata tc                                                          22

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
gatgagcatg gaggaagcgt g                                                           21

<210> SEQ ID NO 27

-continued

<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
cacgcttcct ccatgctcat c                                                                        21

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
caatgatcaa caacatcatc                                                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
gatgatgttg ttgatcattg                                                                          20

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
gctattctgg ttataacaaa t                                                                        21

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
ctagagggta ccaccaatcc                                                                          20

<210> SEQ ID NO 32
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 32
aacctggcca gtaggagt                                                                            18

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33

-continued

```
acccagaaga ctgtggatgg                                                            20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
tcagctcagg gatgaccttg                                                            20
```